US011409275B2

(12) United States Patent
Ahmad

(10) Patent No.: US 11,409,275 B2
(45) Date of Patent: Aug. 9, 2022

(54) SYSTEMS AND METHODS FOR PREDICTING ENVIRONMENTAL CONDITIONS

(71) Applicant: Talal Ali Ahmad, Bedford, MA (US)

(72) Inventor: Talal Ali Ahmad, Bedford, MA (US)

(*) Notice: Subject to any disclaimer, the term of this patent is extended or adjusted under 35 U.S.C. 154(b) by 76 days.

(21) Appl. No.: 16/801,438

(22) Filed: Feb. 26, 2020

(65) Prior Publication Data

US 2021/0191385 A1 Jun. 24, 2021

Related U.S. Application Data

(60) Provisional application No. 62/950,221, filed on Dec. 19, 2019.

(51) Int. Cl.
*G05B 23/02* (2006.01)
*G01N 33/00* (2006.01)
*G08B 21/14* (2006.01)

(52) U.S. Cl.
CPC ..... *G05B 23/0283* (2013.01); *G01N 33/0034* (2013.01); *G01N 33/0075* (2013.01); *G05B 23/024* (2013.01); *G08B 21/14* (2013.01)

(58) Field of Classification Search
CPC .. G05B 23/0283; G05B 23/024; G08B 21/14; B60H 1/008; F24F 11/62; G01N 33/0075; G01N 33/0034
See application file for complete search history.

(56) References Cited

U.S. PATENT DOCUMENTS

| 7,688,198 | B2 | * | 3/2010 | Amidi | G08B 21/14 |
| | | | | | 340/539.22 |
| 8,155,908 | B2 | * | 4/2012 | Nasle | G05B 23/0297 |
| | | | | | 702/85 |
| 8,886,482 | B2 | * | 11/2014 | Higgins | G05B 15/02 |
| | | | | | 340/870.16 |
| 11,067,718 | B1 | * | 7/2021 | Brett | H04W 4/38 |
| 11,080,982 | B1 | * | 8/2021 | Ennaifar | G01M 3/28 |
| 2004/0012491 | A1 | * | 1/2004 | Kulesz | G08B 21/12 |
| | | | | | 436/100 |

(Continued)

FOREIGN PATENT DOCUMENTS

AU 2011252963 B2 11/2011
CA 2760817 C 2/2016
(Continued)

OTHER PUBLICATIONS

Extended Search Report in European Patent Application No. 20212590.2 dated Apr. 19, 2021.
(Continued)

*Primary Examiner* — Stephanie E Bloss
(74) *Attorney, Agent, or Firm* — Schmeiser, Olsen & Watts LLP; Timothy P. Collins

(57) ABSTRACT

Provided are systems and methods for a predictive analysis system, comprising: at least one first sensor at a first location of interest that receives a first source of sensor data; at least one second sensor at a second location of interest that receives a second source of sensor data; and a predictive data processing device that generates a predictive outcome regarding an anticipated event at the first location of interest in response to an analysis of a combination of the first source of sensor data, the second source of sensor data, and a source of historical data.

9 Claims, 5 Drawing Sheets

(56) References Cited

U.S. PATENT DOCUMENTS

| | | | |
|---|---|---|---|
| 2005/0206506 A1* | 9/2005 | Kulesz | H04M 11/002 |
| | | | 702/23 |
| 2005/0264412 A1* | 12/2005 | Levesque | G08B 21/10 |
| | | | 340/517 |
| 2007/0096896 A1* | 5/2007 | Zingelewicz | G08B 31/00 |
| | | | 340/522 |
| 2013/0174646 A1* | 7/2013 | Martin | F24F 11/62 |
| | | | 73/31.02 |
| 2016/0318368 A1* | 11/2016 | Alger | G08G 1/096725 |
| 2019/0187683 A1* | 6/2019 | Celia | G05B 23/0286 |
| 2021/0232741 A1* | 7/2021 | Ogiso | G01M 3/38 |
| 2022/0018824 A1* | 1/2022 | Hicks | G01W 1/10 |

FOREIGN PATENT DOCUMENTS

| | | |
|---|---|---|
| CN | 104142662 B | 6/2017 |
| WO | 2018048913 A1 | 3/2018 |

OTHER PUBLICATIONS

Deleawe, et al. "Predicting Air Quality in Smart Enviomments," 2010, J. Ambient Intell Smart Environ., No. 2(2), pp. 145-152.

* cited by examiner

SYSTEMS AND METHODS FOR PREDICTING ENVIRONMENTAL CONDITIONS

RELATED APPLICATIONS

This application claims priority to U.S. Provisional Application Ser. No. 62/950,221, filed on Dec. 19, 2019 entitled "SENSORS FOR PREDICTIVE OUTCOME AND MAINTENANCE AND SMART CONTROL," the entirety of which is incorporated by reference herein.

FIELD OF THE INVENTION

The inventive concepts relate generally to data collection for providing a predictive outcome. More specifically, the inventive concepts relate to systems and methods that collect data from one or more geographic locations, analyze the data to predict environmental and air quality conditions and to notify users of a predictive outcome, and alter an output and/or performance of electronic and mechanical devices based on the analyzed data.

BACKGROUND

As modern technology continues to provide improvements in data collection, the manner in which the data is used can be challenging in various applications. For example, sensing technologies can be found to detect the presence of hazardous gas or chemicals. However, a need exists for data collection used to predict with accuracy the possibility of a gas or chemical hazard so that an action can be proactively taken to prevent or mitigate the risk of the hazard from occurring.

SUMMARY

In one aspect, provided is a predictive analysis system, comprising: at least one first sensor at a first location of interest that receives a first source of sensor data; at least one second sensor at a second location of interest that receives a second source of sensor data; and a predictive data processing device that generates a predictive outcome regarding an anticipated event at the first location of interest in response to an analysis of a combination of the first source of sensor data, the second source of sensor data, and a source of historical data.

In some embodiments, the predictive outcome controls a machine potentially impacted by the anticipated event.

In some embodiments, the anticipated event is a chemical or gas hazard.

In some embodiments, the first sensor collects a real-time actual environmental condition at the first location of interest as the first source of sensor data, and the second sensor collects information that is a possible impact on the first source of sensor data.

In some embodiments, the predictive analysis system further comprises an analytics computer that is trained to generate an analytics input to the predictive data processing device in response to performing the analysis of the combination of the first source of sensor data, the second source of sensor data, and a source of historical data.

In some embodiments, the predictive data processing device receives the first source of sensor data as raw data and compares the raw data to the historical data which includes previously collected sources of data from the at least one first sensor to generate the predictive outcome.

In some embodiments, the predictive outcome is constructed and arranged for modifying a displayed object replica to include the predictive outcome.

In another aspect, a predictive data processing device comprises a first input that receives a first source of sensor data from at least one first sensor at a first location of interest; a second input that receives a second source of sensor data from at least one second sensor at a second location of interest; a third input that receives a source of historical data; and a special-purpose processor that generates a predictive outcome regarding an anticipated event at the first location of interest in response to an analysis of a combination of the first source of sensor data, the second source of sensor data, and the source of historical data.

In some embodiments, the predictive outcome controls a machine potentially impacted by the anticipated event.

In some embodiments, the anticipated event is a chemical or gas hazard.

In some embodiments, the special-purpose processor is further constructed and arranged to process an analytics input that includes trained machine learning data generated in response to an analysis performed on the first source of sensor data, the second source of sensor data, and a source of historical data.

In some embodiments, the first input receives the first source of sensor data as raw data and compares the raw data to the historical data which includes previously collected sources of data from the at least one first sensor to generate the predictive outcome.

In some embodiments, the predictive outcome is constructed and arranged for modifying a displayed object replica to include the predictive outcome.

In another aspect, a system that predicts air quality at a location comprises at least one gas or chemical sensor at a first location of interest that receives a first source of sensor data; at least one third party sensor at a second location of interest that receives a second source of sensor data; and a predictive data processing device that generates a predictive outcome regarding a possible gas or chemical hazard at the first location of interest in response to an analysis of a combination of the first source of sensor data, the second source of sensor data, and a source of historical data.

DETAILED DESCRIPTION OF THE EMBODIMENTS

In the following description, specific details are set forth although it should be appreciated by one of ordinary skill that the systems and methods can be practiced without at least some of the details. In some instances, known features or processes are not described in detail so as not to obscure the present invention.

Conventional sensing technologies can predict chemical hazards by detecting chemicals, gasses, from various sensors positioned in various locations of a facility. However, predictive analysis is based on the sensor data alone.

In brief overview, systems and methods in accordance with embodiments of the present inventive concepts collect and process data concerning various environmental conditions to generate a predictive outcome. In addition, the systems and methods can provide an output to other objects related to the environmental conditions that may be otherwise potentially affected by the predictive outcome for changing a status of the other objects.

For example, the inventive concepts can collect data from any device, equipment, sensor, or other physical object at one or more different locations concerning air quality and provide a predictive output concerning the risks of gas and/or chemical hazards or the possibility of a fire or explosion in real-time or near real-time. The predictive output, analysis, or maintenance result is established from different data provided by various data sources, one of which can be the sensor devices, that is processed and executed by an algorithm that generates provide the output and provide status changes to different objects in the environment.

Embodiments of the present inventive concepts may to other industries and applications such as but not limited to manufacturing facilities, petrochemical facilities, smart cities or smart homes, commercial or residential buildings, parking lots, or other indoor or outdoor locations, food and agriculture, unmanned autonomous vehicles such as drones or self-driving vehicles, robotic platforms, and so on that may participate in environments susceptible to forces of nature or other manmade or natural acts.

Figure 1:
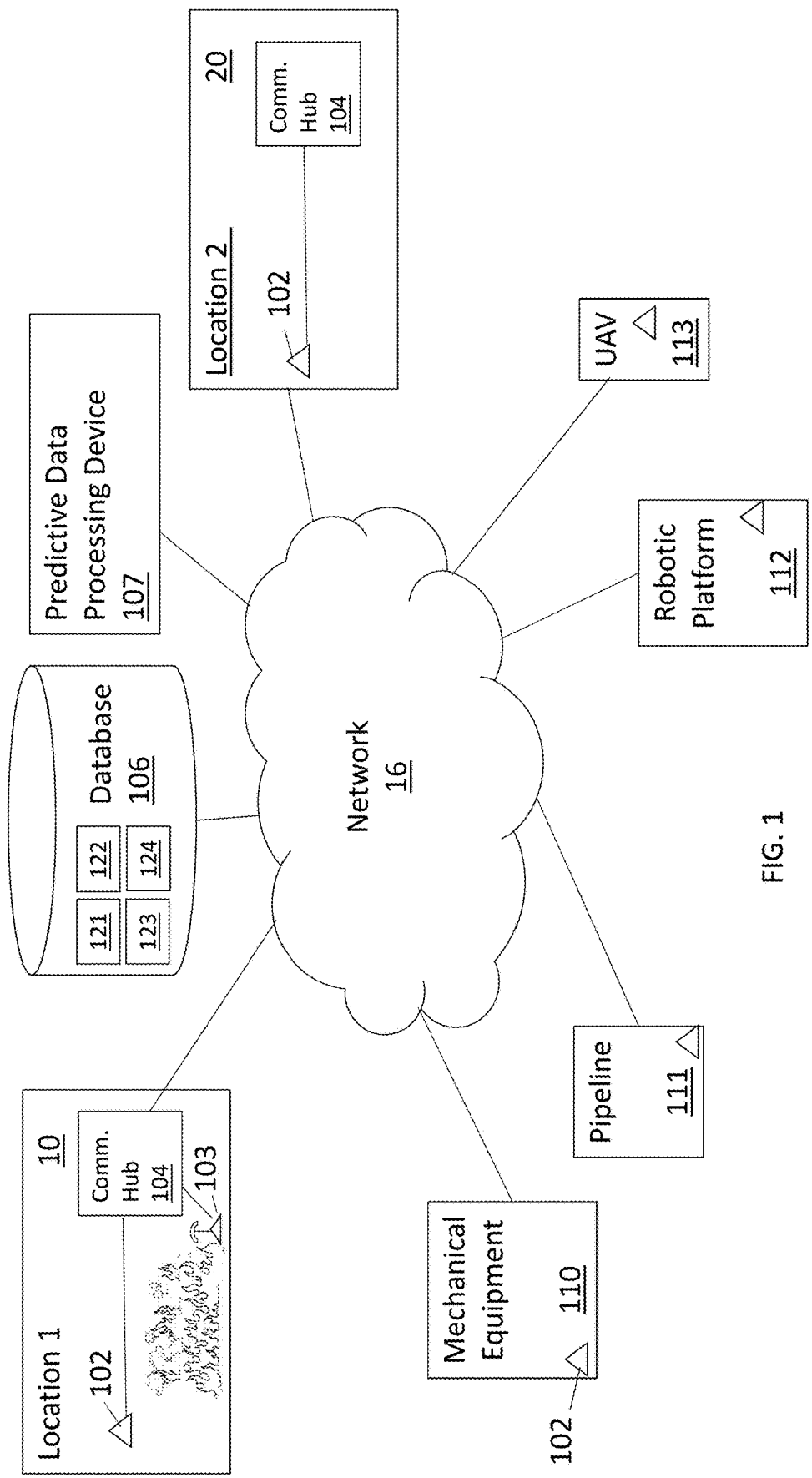
FIG. 1 is a network diagram illustrating an environment in which embodiments of the present inventive concepts can be practiced.

FIG. 1 is a network diagram illustrating an environment in which embodiments of the present inventive concepts can be practiced.

Although FIG. 1 illustrates two locations 10, 20, other embodiments can include one or more locations 10, 20. A location 10, 20 may be a building or outdoor location. In some embodiments, a location 10, 20 may be a region of a machine such as a robotic apparatus or automobile. In some embodiments, a location 10, 20 may a container or cargo that stores objects that produces gas, chemicals, or other emissions detectable by a sensor 102, 103. In some embodiments, a location 10, 20 can include a physical layout that includes one or more sensors 102, 103 that exchanges data with a communication hub 104 via a wired or wireless data link. In some embodiments, one or more sensors (generally, 102, 103) are nanotechnology-based sensors. In other embodiments, one or more sensors are microsensors or picosensors, for example, sensor arrays for nano- and pico-fluidic systems. In some embodiments, elements 102, 103 include Internet of Things (IoT) devices or the like for communicating with the communication hub 104, database 106, and/or predictive data processing device 107. In some embodiments, sensors 102 are gas and/or chemical sensors and sensors 103 are sensors that provide contextual data with respect to data collected by the gas and/or chemical sensors 102, such as wind speed and so on. Accordingly, sensors 102 may be referred to as "first sensors" and sensors 103 may be referred to as "second sensors." Although gas, chemical IoT devices and/or sensors are described, other sensor types for detecting objects, forces, substances, gasses, liquids, and/or solids of interest may equally apply and converting the detection results into electrical signals which can be formatted into data for processing by other elements of the system.

The communication hub 104 in turn can output data collected by the sensors 102, 103 to a remote storage device such as one or more databases 106 via a network 16. The network 16 can be a local area network (LAN), a wide area network (WAN), or other communications network for transmitting electronic data. In some embodiments, network 16 may include cloud computing systems, data center computers, or the like which may include the remote storage device 106 and/or other processor-based devices shown and described in FIG. 1. In some embodiments, a data center of the network 16 may be a private, public, or semi-public hybrid data center that receives and processes data from one or both locations 10, 20, and/or data from other sources used by the predictive data processing device 107 to generate an environmental condition prediction result.

The remote storage device 106 may include one or more databases that store incoming raw data and/or formatted data 121 from various sources. For example, raw data 121 may refer to data that is native or proprietary with respect to a supported data format of the object producing the data. Formatted data on the other hand may refer to raw data that has been converted by a special-purpose computer processor to a different format that is supported by a processor different than that of the originating object, for example, an algorithm embodied in program code that is executed by the predictive data processing device 107. In some embodiments, the incoming data 121 may originate from one or more gas and/or chemical sensors 102 that provide readings of gasses and/or chemicals in the air at the location 10, 20, for example, measured in parts per million (PPM). In some embodiments, a database of the remote storage device 106 receives and stores gas and/or chemical sensor data 121 that can be processed for comparison to other raw data and/or formatted data. For example, other sensors 103 may include wind direction and speed sensors that provide wind conditions at a location 10, 20 where gasses and/or chemicals are detected. In addition to the gas and/or chemical sensor data 121 (in raw or new format), third party or other sensor data, e.g., wind condition data 122 may be received from the include wind direction and speed sensors 103 and stored at the remote storage device 106. In some embodiments, the database receives and stores other data 123 from objects such as local and national weather data, video, static image of equipment, start and end times of a detected source of wind, etc. This other data 123 can be used in combination with gas and/or chemical sensor data to predict environmental conditions. In some embodiments, such data 123 may be generated from a learning algorithm or the like executed by an artificial intelligence computer 13.

In some embodiments, a predictive data processing device 107 processes a combination of sensor and contextual data inputs to present an outcome value 124 to a user. In some embodiments, the outcome value 124 is generated by a machine learning algorithm embodied in program code that is executed by the predictive data processing device 107, and that generates the outcome value 124 in response to a combination of the stored data sets 121, 122, and 123. For example, a gas sensor 102 may provide a ppm value that is processed with other contextual data, e.g., wind and speed sensor data 122 from sensors 103 and stored historical weather condition data 123 to generate a predictive outcome information 124 that is formatted for display on a computer monitor or the like for viewing by a user. In some embodiments, an outcome value 124 is generated by comparing gas and chemical data from different data sources to incoming raw or formatted data. In this case, the system may detect a compound that is not recognized by an IoT device 102. The predictive data processing device 107 takes the incoming sensor data as raw data and compares it to other previously stored raw data, for example, previous sensor results taken in benign conditions at the location 10, 20. In some embodiments, the generated values 124 are stored at the database 106 for subsequent processing. The predictive data processing device 107 may store and execute program code that processes the data using outside data and factors. Outside external factors may apply to collected data received at predictive data processing device 107, for example, external environmental conditions that are unrelated to those conditions at a location of interest, but can nevertheless be combined with other received data to predict an outcome, i.e., generate a predictive outcome information 124. For example, a third-party sensor external to location 10, for example, at location 20 may detect a source of pollen. Other data 122, 123 may provide information that wind conditions flow from location 20 to location 10. The predictive data processing device 107 can generate a predictive outcome information 124 that the pollen will arrive at location 10 at an estimated time based on this combination of data.

One or more machines 110 may be at a location 10, 20, near a location 10, 20, or otherwise in electronic communication with the electronic components such as the sensor(s)102, 103 and/or communication hub 104 of the one or more locations 10, 20. In some embodiments, a machine 110 includes a computer network interface that communicates via the network 16 according to a communication protocol such as TCP/IP, wired or wireless, 3G, 4G, 5G, satellite, and so on. A machine 110 may include but not be limited to mechanical equipment for manufacturing for producing items such equipment, chemical and gas processing units, solid material processors that evaporates gas and chemical in the air, food processing machinery, and so on. Accordingly, some embodiments of the inventive concepts include the presence of sensors 102, 103 at various locations 10, 20, but the sensor data is not processed at the locations 10, 20 but is instead output via the network 16 to the predictive data processing device 107 located at a different centralized location, such as a cloud computing environment or other remote location. A machine 110 can also include sensors 102 and/or 103 for collecting sensor data to be compared with the data at locations 10, 20. In some embodiments, the machine 110 has at least one hardware computer processor for exchanging data with the predictive data processing device 107 and/or other controllers for performing an operation in response to an environmental condition prediction result generated by the predictive data processing device 107.

An example machine 110 may be a tractor that spreads a fertilizer about a farm. The sensor 102 on the tractor 110 may detect the presence of a dangerous chemical in the fertilizer. This sensor data can be compared at the predictive data processing device 107 to historical data regarding the source of fertilizer used in addition to real-time sensor data from a location 10 where the fertilizer is produced to establish that a risk is possible that the fertilizer plant 10 is producing fertilizer with a high quantity of the dangerous chemical.

In addition, or alternatively, the environment described in FIG. 1 according to some embodiments may include objects other than the machine 110 such as gas or chemical pipelines 111 or the like, a robotic platform 112, a manual or unmanned vehicle 113 having a battery that is prone to environmental hazards, and/or other physical objects. Objects 110-113 may be configured with a sensor similar to or different than the sensors 102, 103 at the locations 10, 20. In some embodiments, the predictive data processing device 107 can output a computer command to one or more of the machines 110-113 to control or adjust their output and performance according to data, such as sensor data received by the predictive data processing device 107.

Figure 2:
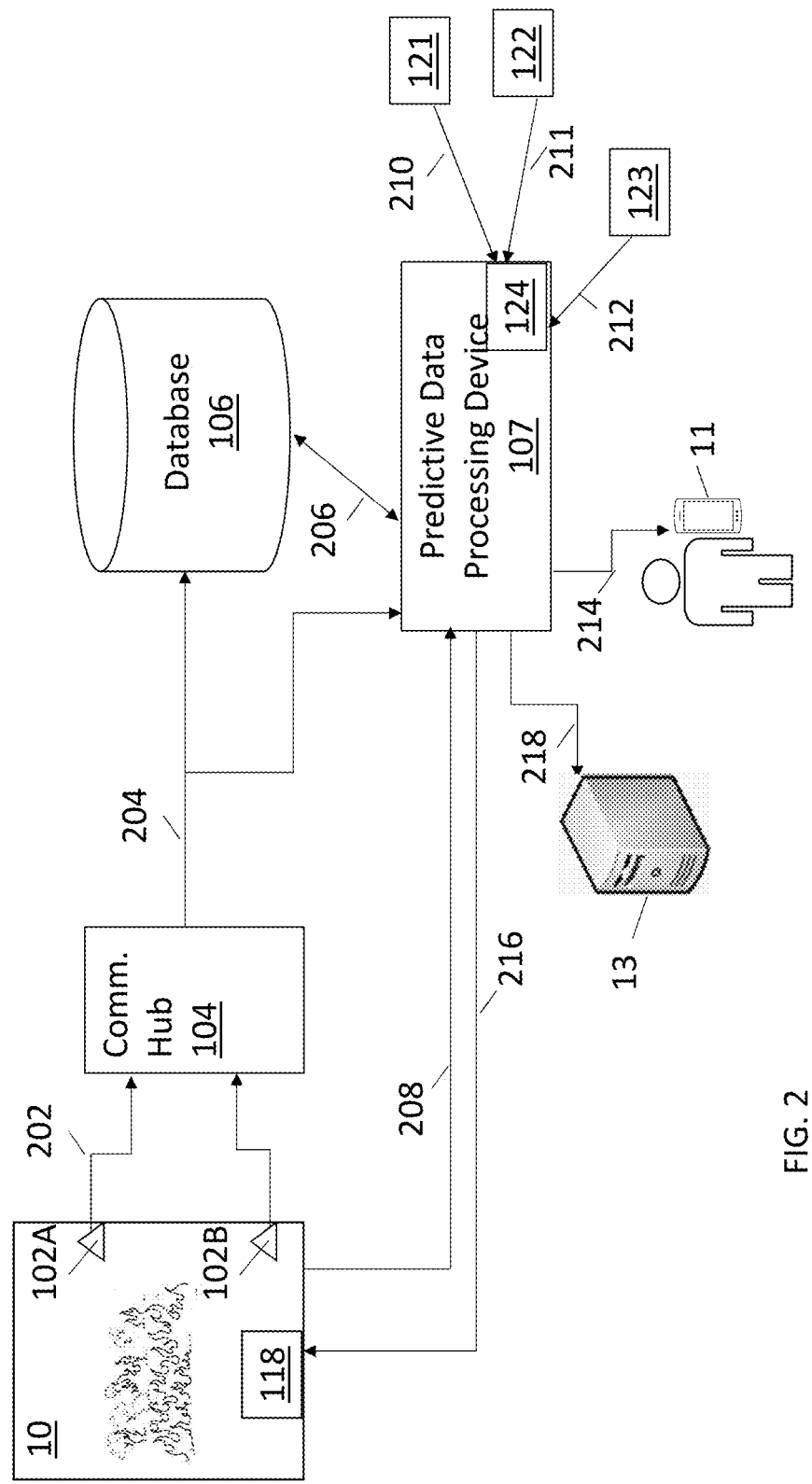
FIG. 2 is a schematic diagram illustrating a single-location system for predicting environmental conditions, in accordance with some embodiments.

FIG. 2 is a schematic diagram illustrating a single-location system for predicting environmental conditions, in accordance with some embodiments. Although FIG. 2 describes a single location 10, other embodiments can include multiple locations, for example, both locations 10 and 20 described in FIG. 1.

The location 10 may include at least one gas sensor 102A and at least one chemical sensor 102B that detect in real-time a gas and/or chemical at the location, convert the detection results into electronic data, and output (202) the electronic sensor data via a communication hub 104 to the network 16. The communication hub 104 can communicate via the data link and/or network 16 using one or more different communication protocols and/or related technologies such as but not limited to Ethernet, TCP/IP, message queue telemetry transport (MQTT) virtual private network (VPN), radio frequency (RF), Bluetooth™, satellite, and/or other data network communication between the IoT sensor 102 and the hub 104. The communication hub 104 can in turn output (204) the data to the database 106 and/or predictive data processing device 107 using one or more network computing technologies such as Zigbee, Zwave, LoRan, Wi-Fi, 3G, 4G, 5G technology, satellite or the like to the network 16 to a network cloud or other location, for example, a location that situates the database 106 and predictive data processing device 107 using public internet and/or private links. The communication hub 104 may communicate with the database 106 to store the sensor data. The communication hub 104 may communicate with the predictive data processing device 107 to provide the sensor data to the predictive data processing device 107 in situations where the database 106 does not receive the sensor data.

The predictive data processing device 107 communicates (206, 208, 210) with the database 106 and/or the other data sources 110-113 to analyze the inputs generated (210, 211, 212) from collected sensor data, e.g., data 121 gas/chemical sensors 102 and context information 122 from sensors 103, and historical data 123. An outcome value 124 can be generated by the predictive data processing device 107, and output (214, 218) to a user computer 11, 13. For example, a first communication connection (206) may include a data exchange between the predictive data processing device 107 and the database 106 to process stored sensor data 121-124, for example, a combination of stored historical environment data concerning weather patterns at a location 10, sensor data 121 concerning traces of a gas or chemical currently at the location, and sensor data 122 concerning a current temperature or wind speed detected at the location 10. Some or all of this data, such as sensor data 121, 122 may be received directly by a second communication connection (208) from the location 10 by instead of or in addition to the database 106. In some embodiments, some or all of this data is received from a mechanical device 110-113. A third communication connection (210) may provide other data, such as raw and/or formatted data, for comparison by the predictive data processing device 107 to the actual sensor data collected at the location. A fourth communication connection (212) may provide other collected data 123 in real time or near real time that is also processed by the predictive data processing device 107 to generate a predictive outcome value 124.

The predictive outcome value 124 can be generated in one or more different formats, and can include different data depending the type of output of the predictive data processing device 107. A first output (214) can be output to a user, in particular, a user computer 11 having a display or other output devices for providing data related to the predictive outcome value 124 in a visual, audio, and/or tactile manner. For example, the outcome value 124 may be converted by the predictive data processing device 107 to a format that permits the user to know at an early stage of a predictive outcome such as possible air quality issues, chemical leakage, or an accident, plus the time will take for the area at the location 10, 20 becomes dangerous zone. In some embodiments, the first output (214) provides an action directly to users. For example, a user is provided with set of instructions to prevent the outcome or protect the user. Such an action could include an inactivation or a shutdown of specific machinery, repairing specific machinery, or generating a time estimate regarding the environmental conditions at the location. In the latter example, the predictive outcome value 124 may be in the form of an electronic text message or other data communication that notifies a recipient of an imminent danger regarding possible high radiation levels at the location 10 due to the predictive data processing device 107 receiving data concerning wind conditions, high radiation levels detected at a nearby location, analytic processing, and so on. According to the processing result, the user may be further notified that persons at the location 10 may be safe for 1 hour before the radiation reaches the location 10.

A second output (216) can be a computer command or the like to other devices to alter their output and performance. For example, the second output (216) may include a status change request that is output to the location 10 where gas or chemical is detected. In this example, a carbon dioxide sensor 102A may sense a presence of a low but not dangerous level of carbon dioxide. However, a second sensor at a furnace 118 at the location may detect a gas flow pipe 111 that is fragile and at risk of forming a hole from which carbon dioxide may possibly escape. This collection of data may be processed whereby the predictive data processing device 107 outputs (216) an electronic request directly to the furnace 118 including an instruction to automatically inactivate the furnace 118.

A third output (218) can include the predictive outcome value 124 in a format suitable for receipt and processing by a third-party analytics, machine learning, deep learning, or other artificial intelligence computer 13, and so on. The computer 13 may contribute to training the p inputs at various times to train the predictive data processing device 107 with respect to machine learning, deep learning, and the like, for example, where the computer 13 deploys a trained AI model.

Figure 3:
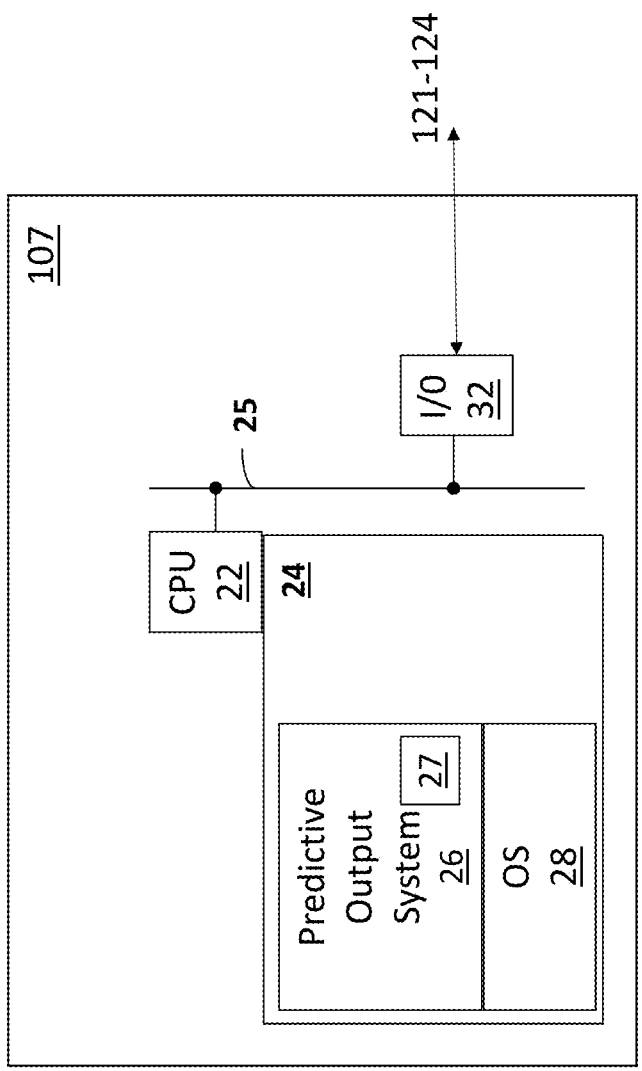
FIG. 3 is a block diagram of a predictive data processing device, in accordance with some embodiments.

FIG. 3 is a block diagram of the predictive data processing device 107 described in FIGS. 1 and 2. The predictive data processing device 107 includes a processor such as a CPU 22, a memory 24, and input/output (I/O) logic 32, for example, a network interface card (NIC), which communicate with each other via a data/control bus and/or data connector 25, for example, a peripheral component interconnect (PCI) bus. The I/O logic 32 can include one or more adaptors for communicating with the network 16.

The memory 24 can include volatile memory, for example, random access memory (RAM) and the like, and/or non-volatile memory, for example, read-only memory (ROM), flash memory, and the like. The memory 24 can include removable and/or non-removable storage media implemented in accordance with methods and technologies known to those of ordinary skill in the art for storing data. Stored in the memory 24 can include program code, such as program code of an operating system (OS) 28 executed by the processor 22.

The memory 24 also includes a predictive output system 26, which receives and processes via the I/O logic 32 one or more data inputs 121, 122, 123 described herein, and generates a predictive output 124 described herein. The predictive output system 26 may include a correlation analyzer 27 that correlates captured sensor data with other data captured from the same geographic area 10, 20 and/or nearby area to produce a prediction result 124. In some embodiments, the correlation analyzer 27 includes artificial intelligence technology or the like for communicating with the artificial intelligence or machine learning computer 13, for example, so that the computer 13 can execute a learning algorithm, or simulation e.g., for AI training with respect to contributing to the generation of the predictive output 124.

Figure 4:
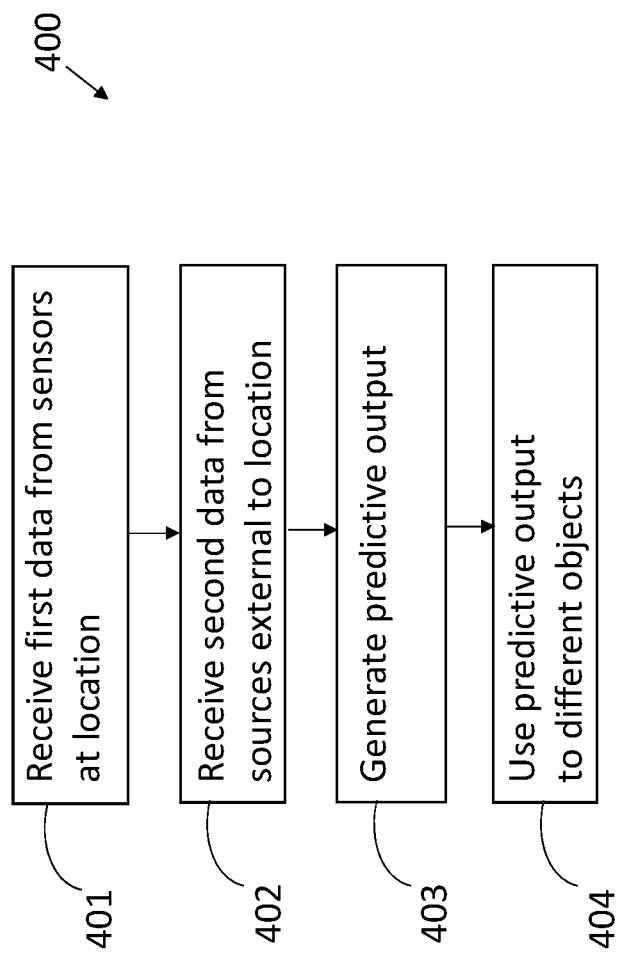
FIG. 4 is a flow diagram illustrating a method for predicting an environmental condition, in accordance with some embodiments.

FIG. 4 is a flowchart illustrating a method 400 for predicting an environmental condition, in accordance with some embodiments. Some or all of the method 400 can include steps performed in electronic components described in FIGS. 1-3. For example, some or all of the method 400 may comply with an algorithm embodied in program code that is executed by the predictive data processing device 107 described in FIGS. 1-3, for example, performed by the predictive output system 26 in FIG. 3.

At block 401, a set of first data is received from one or more sensors 102 at a location.

At block 402, a set of second data is received from one or more sources that are external to the location where the sensors 102 are located.

At block 403, a predictive output is generated from a combination of the first and second data, which in turn is generated by different sources, sensors, historical data and real-time data. In some embodiments, the predictive output includes data about the possibility of a gas, chemical, fire, explosion, or other hazard in real-time or near real-time.

At block 404, the predictive output is applied to one or more machines. Method 400 can apply to various applications. For example, as described herein, some embodiments include a location 10 that includes at least one chemical sensor 102B that detect a chemical. Here, the predictive outcome value 124 determined from the detection of chemicals of the sensor 102B may include data corresponding to a chemical hazard outbreak prediction at the location 10, or a different geographic area or enclosed area. The chemical hazard outbreak predictive output 404 may include time left to reach a symptoms level, time left to reach a critical level, and/or other information used to provide time-related prediction information. Another predictive output 404 may pertain to the direction that a hazardous chemical is traveling based on collected information from the location sensors or other sources such as online meteorological data such as temperature, wind direction, and wind speed.

In a related example, equipment performance may result in an increase in air pollution at the location 10. The predictive output 404 may provide an assessment on how the location 10 may be affected based on the collected information from the location sensors or other sources such as online meteorological data such as temperature, wind direction, and wind speed. The predictive output 404 may be output as electronic signals, e.g., data, to the equipment that controls the equipment to perform differently to reduce the air pollution, for example, reduce a speed of operation which in turn results in less emissions by the equipment.

In another example, the method 400 may be applied to gas or chemical leaks in a petroleum pipeline 111 (see FIG. 1) so that a predictive output 404 predicts a speed or quantity of a given pipeline leak. For example, known historical data may establish that carbon monoxide levels at the pipeline 111 are at a threshold level. However, sensors 102 may detect a current carbon monoxide level that is greater than the threshold level. The system can output instructions to the sensors 102 to collect carbon monoxide readings along the pipeline 111 to determine the location of a leak causing the increased carbon monoxide readings. Wind conditions can be determined from second sensors 103 and used by the predictive data processing device 107 to predict that the high readings are downstream from the actual location of the leak.

In another example, the method 400 may be applied to a battery to predict an operating lifespan of the battery by correlating gas or chemical leaks and the age of the battery.

In another example, the method 400 may detect the composition of a chemical of interest using artificial intelligence technology, for example, artificial intelligence computer 13, as well as the first and second data of steps 401 and 402 respectively. For example, historical data such as safe levels of the chemical of interest may be used to train the artificial intelligence computer 13, for example, processed with data regarding current levels of the chemical of interest for generating a predictive output 404. The system can therefore rely on historical data instead of feedback when generating the predictive output.

In another example, the method 400 may be applied in the food industry and agriculture. For example, a sensor 102 may detect the odor of fruit, or an analyte sensor may predict if the food cooked correctly correlated with cooking time and temperature. This sensor data can be processed so that the system 107 predicts the time left to stay viable and fresh while in storage or transport.

In another example, the system 107 may process environment data and predict the shelf time for produce, livestock, and dairy.

Figure 5:
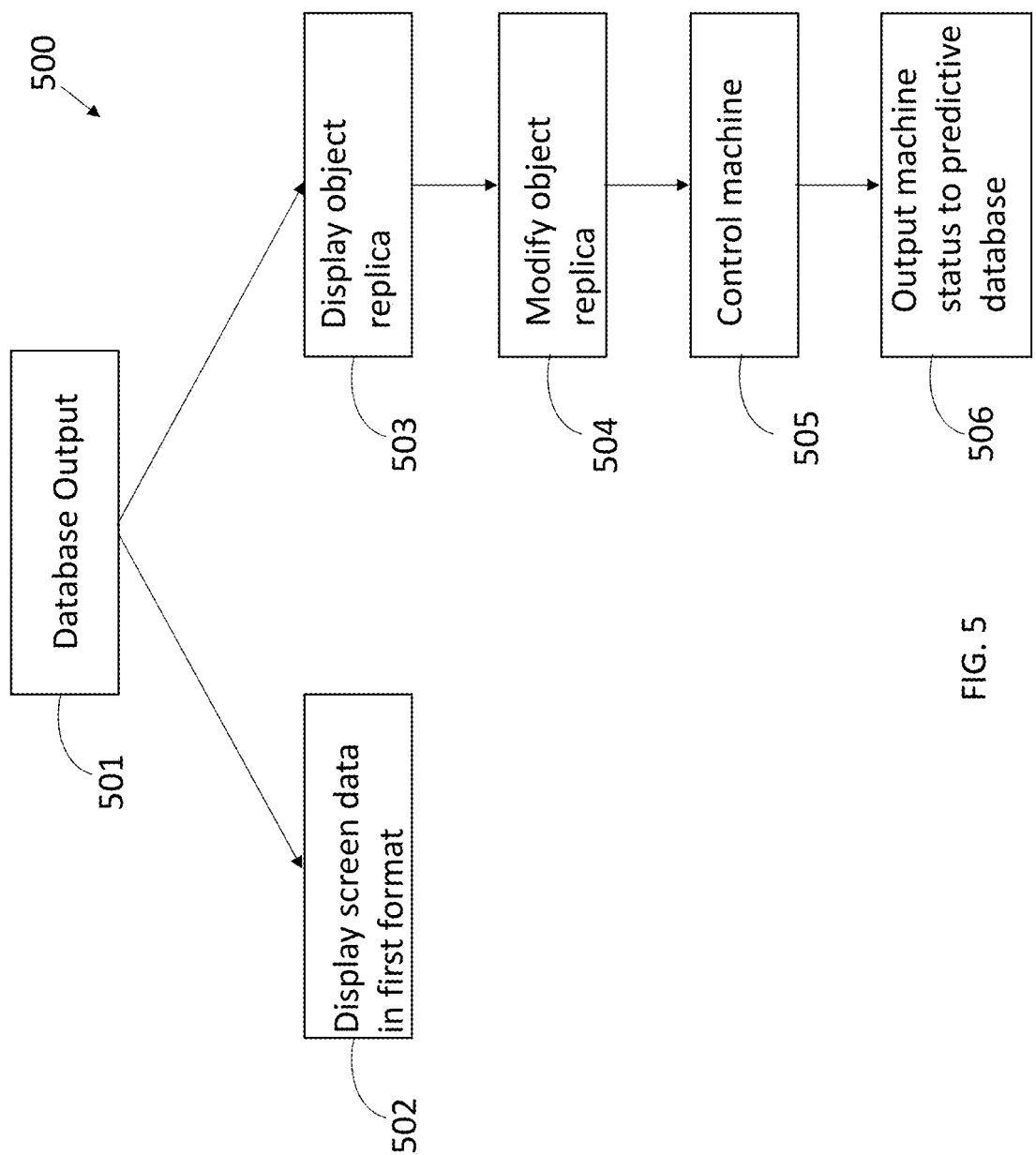
FIG. 5 is a flow diagram illustrating a method for electronic digital replication and display of an object impacted a real or predicted environmental condition, in accordance with some embodiments.

FIG. 5 is a flow diagram illustrating a method 500 for electronic digital replication and display of an object impacted a real or predicted environmental condition, in accordance with some embodiments. Some or all of the method 500 can include steps performed in electronic components described in FIGS. 1-3. For example, some or all of the method 500 may comply with an algorithm embodied in program code that is executed by the predictive data processing device 107 described in FIGS. 1-3, for example, performed by the predictive output system 26 in FIG. 3. Some or all of the method 500 may be executed on a computer display.

As described above, embodiments may include a database 106 that stores a combination of raw data and/or formatted data 121 and other sensor data 122 from various sources, historical data 123, and predictive outcome information 124. At block 501, this data may be output from the database 106. At block 502, the data output from the database 106 may be formatted for a display screen, referred to as a first format. For example, the data may be an outcome value 124 generated by the predictive data processing device 107, in the form of values, charts, text information, or the like that notifies a reader of a predictive event, for example, described by way of example in a foregoing embodiment.

At block 503, the data output from the database 106 may be formatted as a display replica of an object to which a predictive event corresponds, referred to as a second format. The object to be displayed may be a machine 110 or other object 111-113 shown and described with regard to FIGS. 1-4. A two-dimensional or three-dimensional image or representation of the object is displayed on a computer display. The display replica can be generated by a computer graphics system or other well-known electronic apparatus for generating computer graphics. Along with the display replica of the object, a visual, audio, or tactile marker can be generated that identifies a location of a predictive event, for example, location on a pipeline 111 where a crack may be determined based on a predictive result generated by the predictive data processing device 107 due to a sensed increase in gas emitted from the pipeline.

In some embodiments, the display replica is generated by a special-computer software application constructed and arranged to communicate with a computer display such as a monitor to display the outcome on a digital replica of living and non-living physical entities, e.g., human body, machinery, city, and building, for example, at location 10 or 20. A three-dimensional replica can display the output within the replica. For example, if a fan of machinery is reporting an issue, it will turn the color of the fan red. The user will have the ability to manipulate the replica but digital removing other attached parts to see another area on the replica. The user using input devices, keyboards, touch screen or hand gestures to simulate the replica by sending new input to the replica and observe the outcome using the replica. The new input data will be sent to the predictive application and run. It is processed and provides the output on the replica.

Furthermore, a replica will display an output of a simulation that displays the output from a combination of real-time data, historical data, and other related data used by the system to generate the predictive output.

At block 504, a user can modify the display replica, for example, using a mouse or other input/output device to select the visual mark to zoom in on a region of the display replica. For example, an object replica may be a map of a location 10 or a three-dimensional representation of a pipeline 111. A user can modify the display to zoom in on a map of the location 10 or remove a layer of the displayed representation of the pipeline to identify a specific region of a predictive event, such as a location of a gas leak.

At block 505, a user can use a display replica to control a machine or object. For example, an automobile may be running in a garage or other enclosed area, thereby generating high carbon monoxide levels. However, a carbon monoxide detector in a second floor bedroom has not yet detected carbon monoxide. The predictive data processing device 107 may generate a predictive outcome value 124 regarding the imminent arrival in the second floor bedroom of the carbon monoxide and notify the occupants of this predictive event. A user can view a digital display replica of the automobile and select the ignition switch displayed on the automobile to shut the automobile off. Other examples may include the ability to control a machine 110 by touching the displayed object to alter a state of the machine, increase or decrease a function of the machine, and so on.

At block 506, a new machine status can be generated and output to the predictive database 106, for example, as stored data 124. The predictive data processing device 107, which in some embodiments may be part of the database 106, can generate a new output based on this new machine status data. An example of an operation that includes this new generated data may be that the replica of a machine indicates that the status of all machine functions is satisfactory, and the elements of the machine are correctly operating. The generated output can be output to and stored at the database 106.

As previously described, a computer system described with reference to the figures herein may generally comprise a processor, an input device coupled to the processor, an output device coupled to the processor, and memory devices each coupled to the processor. The processor may perform computations and control the functions of the system, including executing instructions included in computer code for the tools and programs capable of implementing methods for allocating trailers and loading docks, in accordance with some embodiments, wherein the instructions of the computer code may be executed by the processor via a memory device. The computer code may include software or program instructions that may implement one or more algorithms for implementing one or more of the foregoing methods, techniques, algorithms, and the like. The processor executes the computer code.

The memory device may include input data. The input data includes any inputs required by the computer code. The output device displays output from the computer code. A memory device may be used as a computer usable storage medium (or program storage device) having a computer-readable program embodied therein and/or having other data stored therein, wherein the computer-readable program comprises the computer code. Generally, a computer program product (or, alternatively, an article of manufacture) of the computer system may comprise said computer usable storage medium (or said program storage device).

As will be appreciated by one skilled in the art, in a first embodiment, the present invention may be a method; in a second embodiment, the present invention may be a system; and in a third embodiment, the present invention may be a computer program product. Any of the components of the embodiments of the present invention can be deployed, managed, serviced, etc. by a service provider that offers to deploy or integrate computing infrastructure with respect to embodiments of the inventive concepts. Thus, an embodiment of the present invention discloses a process for supporting computer infrastructure, where the process includes providing at least one support service for at least one of integrating, hosting, maintaining and deploying computer-readable code (e.g., program code) in a computer system including one or more processor(s), wherein the processor(s) carry out instructions contained in the computer code causing the computer system for generating a technique described with respect to embodiments. Another embodiment discloses a process for supporting computer infrastructure, where the process includes integrating computer-readable program code into a computer system including a processor.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer-readable program instructions.

These computer-readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other device to produce a computer-implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

A number of implementations have been described. Nevertheless, it will be understood that the foregoing description is intended to illustrate, and not to limit, the scope of the inventive concepts which are defined by the scope of the claims. Other examples are within the scope of the following claims.

What is claimed is:
1. A predictive analysis system, comprising:
 at least one first sensor at a first location of interest that receives a first source of sensor data including information about a real-time actual environmental condition at the first location of interest;
 at least one second sensor at a second location of interest that receives a second source of sensor data including contextual data with respect to the first source of sensor data and information that is a possible impact on the first source of sensor data;

a predictive data processing device that generates a predictive outcome regarding an anticipated event pertaining to the real-time actual environmental condition at the first location of interest in response to an analysis of a combination of the first source of sensor data, the contextual data of the second source of sensor data, and a source of historical data, the predictive outcome including a combination of data, for a machine or object impacted by the anticipated event, data so that the machine or object is operational to react to the anticipated event, the predictive outcome including a prediction time of occurrence of the anticipated event pertaining to the real-time actual environmental condition; and a computer graphics system for generating a display replica of the machine or object to which the predictive outcome corresponds and further identifying a location of the anticipated event on the display replica, the display replica further displaying an output of a simulation from the combination of the first source of sensor data, the contextual data of the second source of sensor data, and the source of historical data used by the system to generate the predictive output, the display replica controlling the machine or object to be operational to react to the anticipated event.

2. The predictive analysis system of claim 1, wherein the anticipated event is a chemical or gas hazard.

3. The predictive analysis system of claim 1, further comprising an analytics computer that is trained to generate an analytics input to the predictive data processing device in response to performing the analysis of the combination of the first source of sensor data, the second source of sensor data, and the source of historical data.

4. The predictive analysis system of claim 1, wherein the predictive data processing device receives the first source of sensor data as raw data and compares the raw data to the historical data which includes previously collected sources of data from the at least one first sensor to generate the predictive outcome.

5. A predictive data processing device, comprising:
a first input that receives a first source of sensor data from at least one first sensor at a first location of interest including information about a real-time actual environmental condition at the first location of interest;
a second input that receives a second source of sensor data from at least one second sensor at a second location of interest, the second source of sensor data including contextual data with respect to the first source of sensor data and information that is a possible impact on the first source of sensor data;
a third input that receives a source of historical data; and
a special-purpose processor that generates a predictive outcome regarding an anticipated event pertaining to the real-time actual environmental condition at the first location of interest in response to an analysis of a combination of the first source of sensor data, the contextual data of the second source of sensor data, and the source of historical data, the predictive outcome including a combination of data for a machine or object impacted by the anticipated event, data so that the machine or object is operational to react to the anticipated event, and data for displaying information regarding the machine or object impacted by the anticipated event, the predictive outcome including a prediction time of occurrence of the anticipated event pertaining to the real-time actual environmental condition, the special-purpose processor further generating for a display a display replica of the machine or object to which the predictive outcome corresponds and further identifying a location of the anticipated event on the display replica, the display replica further displaying an output of a simulation from the combination of the first source of sensor data, the contextual data of the second source of sensor data, and the source of historical data used to generate the predictive output, the display replica controlling the machine or object to be operational to react to the anticipated event.

6. The predictive data processing device of claim 5, wherein the anticipated event is a chemical or gas hazard.

7. The predictive data processing device of claim 5, wherein the special-purpose processor is further constructed and arranged to process an analytics input that includes trained machine learning data generated in response to an analysis performed on the first source of sensor data, the second source of sensor data, and the source of historical data.

8. The predictive data processing device of claim 5, wherein the first input receives the first source of sensor data as raw data and compares the raw data to the historical data which includes previously collected sources of data from the at least one first sensor to generate the predictive outcome.

9. A system that predicts air quality at a location, comprising:
at least one gas or chemical sensor at a first location of interest that receives a first source of sensor data;
at least one third party sensor at a second location of interest that receives a second source of sensor data including contextual data with respect to the first source of sensor data and information that is a possible impact on the first source of sensor data;
a predictive data processing device that generates a predictive outcome regarding a possible gas or chemical hazard at the first location of interest in response to an analysis of a combination of the first source of sensor data, the contextual data of the second source of sensor data, and a source of historical data, the predictive outcome including a combination of data for a machine or object impacted by the possible gas or chemical hazard, data so that the machine or object is operational to react to the possible gas or chemical hazard, and data for displaying information regarding the machine or object impacted by the possible gas or chemical hazard, the predictive outcome including a prediction time of occurrence of the possible gas or chemical hazard; and
a computer graphics system for generating a display replica of the machine or object to which the predictive outcome corresponds and further identifying a location of the possible gas or chemical hazard on the display replica, the display replica further displaying an output of a simulation from the combination of the first source of sensor data, the contextual data of the second source of sensor data, and the source of historical data used by the system to generate the predictive output, the display replica controlling the machine or object to be operational to react to the possible gas or chemical hazard.

* * * * *